(12) United States Patent
Zhao et al.

(10) Patent No.: US 11,883,822 B2
(45) Date of Patent: Jan. 30, 2024

(54) REACTION DEVICE FOR DETECTION CHIP AND REACTION SYSTEM

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zijian Zhao, Beijing (CN); Mengjun Hou, Beijing (CN); Yudan Yin, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 419 days.

(21) Appl. No.: 17/254,984

(22) PCT Filed: Mar. 31, 2020

(86) PCT No.: PCT/CN2020/082402
§ 371 (c)(1),
(2) Date: Dec. 22, 2020

(87) PCT Pub. No.: WO2020/207295
PCT Pub. Date: Oct. 15, 2020

(65) Prior Publication Data
US 2021/0268504 A1    Sep. 2, 2021

(30) Foreign Application Priority Data
Apr. 9, 2019  (CN) .......................... 201920470599.3

(51) Int. Cl.
*B01L 3/00*   (2006.01)
*B01L 7/00*   (2006.01)
*G01N 21/64*  (2006.01)

(52) U.S. Cl.
CPC ......... *B01L 3/502784* (2013.01); *B01L 7/525* (2013.01); *G01N 21/6456* (2013.01);
(Continued)

(58) Field of Classification Search
CPC ............... B01L 3/502784; B01L 7/525; B01L 2200/148; B01L 2300/0816;
(Continued)

(56) References Cited

U.S. PATENT DOCUMENTS 10,301,676 B2    5/2019  Yan et al.
2002/0001848 A1  1/2002  Bedingham et al.
(Continued)

FOREIGN PATENT DOCUMENTS

CN    105861293 A    8/2016
CN    106222068 A   12/2016
(Continued)

OTHER PUBLICATIONS

Extended European Search Report issued in European Application No. 20787410.8, which has an issue dated Jan. 5, 2023.
(Continued)

*Primary Examiner* — Jennifer Wecker
*Assistant Examiner* — Kathryn Elizabeth Limbaugh
(74) *Attorney, Agent, or Firm* — Dilworth & Barrese, LLP.; Michael J. Musella, Esq.

(57) ABSTRACT

A reaction device for a detection chip and a reaction system are provided. The reaction device includes a chip carrier and an electrical signal control unit. The chip carrier is configured to place and fix the detection chip; and the electrical signal control unit is configured to apply an electrical signal to the detection chip so as to drive a heating electrode of the detection chip.

18 Claims, 7 Drawing Sheets

(52) U.S. Cl.
CPC .... *G01N 21/6486* (2013.01); *B01L 2200/148* (2013.01); *B01L 2300/0816* (2013.01); *B01L 2300/0867* (2013.01); *B01L 2300/1827* (2013.01); *B01L 2400/0487* (2013.01)

(58) Field of Classification Search
CPC ..... B01L 2300/0867; B01L 2300/1827; B01L 2400/0487; G01N 21/6456; G01N 21/6486
See application file for complete search history.

(56) References Cited

U.S. PATENT DOCUMENTS

| | | | |
|---|---|---|---|
| 2012/0052560 A1 | 3/2012 | Knight et al. | |
| 2015/0140562 A1 | 5/2015 | Conoci et al. | |
| 2015/0328633 A1 | 11/2015 | Yoo | |
| 2016/0051985 A1* | 2/2016 | Knight | B01L 3/502746 435/286.1 |
| 2019/0168223 A1* | 6/2019 | Soto-Moreno | H01L 21/768 |

FOREIGN PATENT DOCUMENTS

| | | |
|---|---|---|
| CN | 109234158 A | 1/2019 |
| CN | 109289949 A | 2/2019 |
| CN | 209974747 U | 1/2020 |
| WO | 03/087410 A1 | 10/2003 |
| WO | 2019/046860 A1 | 3/2019 |

OTHER PUBLICATIONS

Extended European search report issued by the European Patent Office in application No. 21783122.1 dated Sep. 11, 2023.

* cited by examiner

REACTION DEVICE FOR DETECTION CHIP AND REACTION SYSTEM

The present application claims the priority of Chinese patent application No. 201920470599.3, filed on Apr. 9, 2019, the entire disclosure of which is incorporated herein by reference as part of the disclosure of this application.

TECHNICAL FIELD

Embodiments of the present disclosure relate to a reaction device for a detection chip, and a reaction system.

BACKGROUND

Polymerase chain reaction (PCR) is a molecular biology technique used for amplifying specific DNA (deoxyribonucleic acid) fragments, which can copy DNA of insignificant amounts to large quantities, so as to greatly increase the amount of DNA.

SUMMARY

At least one embodiment of the present disclosure provides a reaction device for a detection chip, and the reaction device comprises: a chip carrier, configured to place and fix the detection chip; and an electrical signal control unit, configured to apply an electrical signal to the detection chip so as to drive a heating electrode of the detection chip.

For example, the reaction device provided by an embodiment of the present disclosure further comprises a support frame. The chip carrier comprises a bottom plate, a support portion, a limiting groove, and at least one limiting block; the bottom plate comprises a hollow region, and is configured to be in sliding connection with the support frame; the support portion is in the hollow region of the bottom plate, and is configured to support the detection chip; the limiting groove is around the hollow region of the bottom plate, and is configured to prevent shift of the detection chip; and the limiting block is on at least one side of the limiting groove, and is configured to prevent warping of the detection chip.

For example, in the reaction device provided by an embodiment of the present disclosure, the chip carrier further comprises a clamp, and the clamp is configured to be capable of moving close to or away from the support portion, so as to allow the detection chip to be at a fixed position or a variable position relative to the support portion.

For example, the reaction device provided by an embodiment of the present disclosure, the clamp comprises a contact electrode, the contact electrode is configured to be capable of being in contact with a control electrode of the detection chip to realize electrical connection, and the electrical signal control unit is electrically connected to the contact electrode, and is configured to apply the electrical signal to the control electrode of the detection chip through the contact electrode so as to drive the heating electrode of the detection chip.

For example, the reaction device provided by an embodiment of the present disclosure, the bottom plate is further connected to the support frame through a linear guide rail.

For example, the reaction device provided by an embodiment of the present disclosure further comprises a driving motor, and the driving motor is configured to drive the bottom plate to move relative to the support frame.

For example, the reaction device provided by an embodiment of the present disclosure further comprises a temperature sensor. The support portion comprises a groove, and the temperature sensor is in the groove, and is configured to be capable of being in contact with the detection chip so as to sense a temperature of the detection chip.

For example, the reaction device provided by an embodiment of the present disclosure further comprises a cooling unit, and the cooling unit is configured to cool down the detection chip.

For example, in the reaction device provided by an embodiment of the present disclosure, the cooling unit comprises a fan or an air blower.

For example, the reaction device provided by an embodiment of the present disclosure further comprises an optical unit, and the optical unit is configured to perform an optical detection on the detection chip.

For example, in the reaction device provided by an embodiment of the present disclosure, the optical unit comprises: a light source, configured to emit light to illuminate the detection chip; and an image sensor, configured to receive light emitted by the light source and reflected by the detection chip.

For example, in the reaction device provided by an embodiment of the present disclosure, the light source comprises a laser or a fluorescent lamp.

For example, in the reaction device provided by an embodiment of the present disclosure, the image sensor comprises a charge coupled device image sensor.

For example, the reaction device provided by an embodiment of the present disclosure further comprises an interaction unit, and the interaction unit is configured to interact with a user.

For example, in the reaction device provided by an embodiment of the present disclosure, the interaction unit comprises a touch screen, and the touch screen is configured to display and perform a touch detection to obtain an input instruction of the user; or the interaction unit comprises a display screen and a button, the display screen is configured to display, and the button is configured to obtain an input instruction of the user.

For example, the reaction device provided by an embodiment of the present disclosure further comprises a control unit, and the control unit is configured to control a working state of the reaction device.

For example, the reaction device provided by an embodiment of the present disclosure further comprises a storage unit, and the storage unit is configured to store detected data and/or a work log of the reaction device.

For example, the reaction device provided by an embodiment of the present disclosure further comprises a power supply, and the power supply is configured to supply power to the reaction device.

At least one embodiment of the present disclosure further provides a reaction system, and the reaction system comprises the reaction device for the detection chip provided by any one of the embodiments of the present disclosure and at least one detection chip. The detection chip comprises a plurality of micro-reaction chambers, and the micro-reaction chambers are capable of containing reaction system solution; and the electrical signal control unit of the reaction device is configured to apply the electrical signal to the detection chip to heat up the detection chip, and a cooling unit of the reaction device is configured to cool down the detection chip, so as to allow the reaction system solution to perform temperature cycle comprising a refolding phase, an annealing phase, and an extending phase.

For example, in the reaction system provided by an embodiment of the present disclosure, an optical unit of the reaction device is configured to perform an optical detection on the detection chip so as to obtain a fluorescent image.

BRIEF DESCRIPTION OF THE DRAWINGS

In order to clearly illustrate the technical solutions of the embodiments of the present disclosure, the drawings of the embodiments will be briefly described in the following. It is obvious that the described drawings are only related to some embodiments of the present disclosure and thus are not limitative to the present disclosure.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect," "connected," "coupled," etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

Different from traditional PCR technology, digital polymerase chain reaction (digital PCR, dPCR) chip technology is to sufficiently dilute the nucleic acid sample, so that the number of target molecules (i.e., DNA templates) in each reaction unit is less than or equal to one. In each reaction unit, the PCR amplification is performed on the target molecule, and the fluorescent signal of each reaction unit is statistically analyzed after the amplification finishes, so as to realize the absolute quantitative detection of single molecule DNA. Because the dPCR has advantages of high sensitivity, strong specificity, high detection throughput, accurate quantification, and the like, the dPCR is widely used in the fields of clinical diagnosis, gene instability analysis, single-cell gene expression, environmental microorganism detection, prenatal diagnosis, etc.

During the PCR reaction, the double-stranded structure of the DNA fragment refolds at a high temperature to form the single-stranded structure, primers and the single-stranded structure are combined according to the principle of complementary base pairing at a low temperature, base combining extension is realized at the optimal temperature of the DNA polymerase, and the above process is the temperature cycling process of refolding-annealing-extending. The DNA fragment can be replicated in large amounts through a plurality of temperature cycling processes of refolding-annealing-extending.

In order to realize the above temperature cycling process, a series of external equipments may be used to heat and cool the detection chip, so that the volume of the equipment is large, multiple equipments may need to form a complete set, the operation is complicated, and the cost is high. Commercial products usually adopt external equipment for temperature control, and the detection efficiency usually exceeds 60 minutes (20 cycles to 30 cycles), some products even reach 90 minutes to 120 minutes (20 cycles to 30 cycles), so that the detection efficiency is low. Moreover, during the process of heating and cooling the detection chip, the overall temperature of the detection chip changes accordingly, so that the temperature of other structures and components in the detection chip except for the micro-cavity containing the DNA fragment also changes accordingly, thereby increasing risk of damage to components such as circuits.

At least one embodiment of the present disclosure provides a reaction device for a detection chip and a reaction system. The reaction device can realize high-efficiency and accurate temperature control, simple temperature control mode, direct insertion and direct reading, simple operation, high intelligent degree, high portable degree, high integration degree, and high detection efficiency, and can realize efficient and fast digital PCR detection.

Hereinafter, some embodiments of the present disclosure are described in detail with reference to the accompany drawings. It should be noted that the same reference numerals in different drawings are used to refer to the same described elements.

At least one embodiment of the present disclosure provides a reaction device, and the reaction device is used for a detection chip and includes a chip carrier and an electrical signal control unit. The chip carrier is configured to place and fix the detection chip; and the electrical signal control unit is configured to apply an electrical signal to the detection chip so as to drive a heating electrode of the detection chip.

Figure 1:
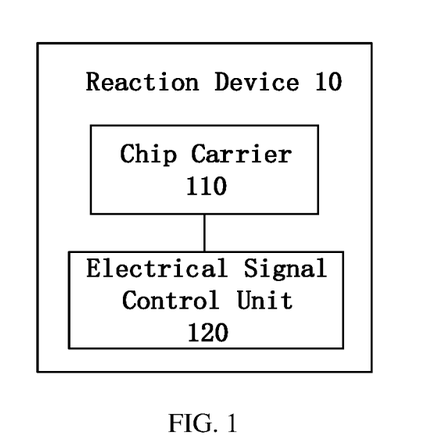
FIG. 1 is a schematic block diagram of a reaction device provided by some embodiments of the present disclosure.

FIG. 1 is a schematic block diagram of a reaction device provided by some embodiments of the present disclosure. As illustrated in FIG. 1, a reaction device 10 includes a chip carrier 110 and an electrical signal control unit 120. For example, the reaction device 10 cooperates with a detection chip additionally provided to realize PCR reaction (for example, PCR detection can be further realized). In the working process, the detection chip contains reaction system solution, and the reaction device 10 is capable of applying the electrical signal to the detection chip so as to heat up the detection chip (for example, a functional region in the detection chip), so that a temperature cycling process of refolding-annealing-extending is performed on the reaction system solution in the detection chip, thereby allowing the DNA fragment in the reaction system solution to be replicated in large amounts.

For example, the chip carrier 110 is configured to place and fix the detection chip, which can realize plug and play of the detection chip. The electrical signal control unit 120 is configured to apply the electrical signal (for example, a voltage signal) to the detection chip so as to drive the heating electrode of the detection chip. After the heating electrode of the detection chip receives the electrical signal, the heating electrode may release heat, so that the functional region of the detection chip is heated to reach a preset temperature for performing the temperature cycling process.

Figure 2:
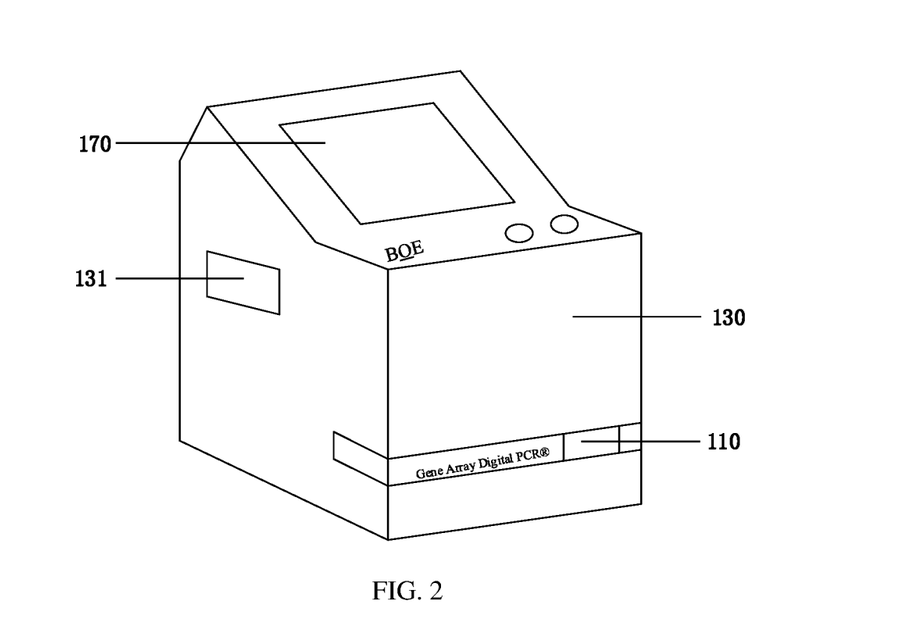
FIG. 2 is a schematic diagram of appearance of a reaction device provided by some embodiments of the present disclosure.

FIG. 2 is a schematic diagram of appearance of a reaction device provided by some embodiments of the present disclosure. As illustrated in FIG. 2, the reaction device 10 further includes a support frame 130. For example, the support frame 130 is the outer shell and internal support structure of the reaction device 10, which plays a role of support, protection, etc., and can also be used to provide installation positions for other components of the reaction device 10. For example, the support frame 130 may be made of plastic, metal or any other suitable materials.

Figure 3:
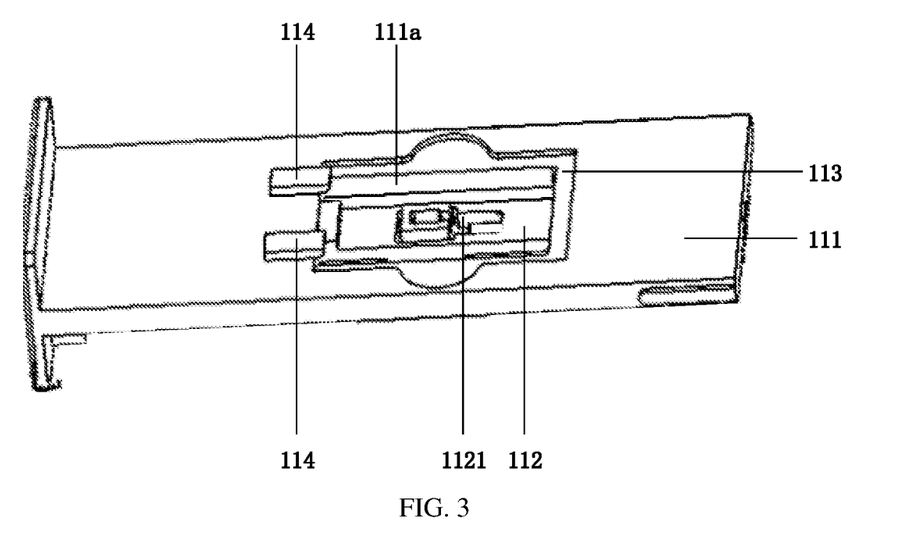
FIG. 3 is a schematic diagram of a chip carrier of a reaction device provided by some embodiments of the present disclosure.

FIG. 3 is a schematic diagram of a chip carrier of a reaction device provided by some embodiments of the present disclosure. As illustrated in FIG. 2 and FIG. 3, the chip carrier 110 is provided on the support frame 130 and is in sliding connection with the support frame 130, so that the chip carrier 110 can be pulled out or pushed into the support frame 130. In the case where the chip carrier 110 is pulled out of the support frame 130, the chip carrier 110 is exposed outside the support frame 130, so that the detection chip can be placed or taken out. In the case where the chip carrier 110 is pushed into the support frame 130, the chip carrier 110 is contained in the inner space of the support frame 130, so that operations such as heating, cooling, and optical detection can be performed.

For example, as illustrated in FIG. 3, the chip carrier 110 includes a bottom plate 111, a support portion 112, a limiting groove 113, and at least one limiting block 114.

For example, the bottom plate 111 is configured to be in sliding connection with the support frame 130, so that the chip carrier 110 can be pulled out or pushed into the support frame 130. For example, the bottom plate 111 may be connected to the support frame 130 through a linear guide rail, and the linear guide rail may be provided on both sides of the bottom plate 111. It should be noted that, in the embodiments of the present disclosure, the connection method of the bottom plate 111 and the support frame 130 is not limited, and may adopt any suitable connection method or any suitable connection structure, which may be determined according to actual requirements.

For example, in some examples, the reaction device 10 may further include a driving motor, and the driving motor is configured to drive the bottom plate 111 to move relative to the support frame 130, so as to realize automatic loading of the detection chip, thereby improving automation degree of the reaction device 10 and reducing manual operations. For example, the driving motor can be connected to a slider in the linear guide rail, the slider is fixedly connected to the bottom plate 111, and a guide rail in the linear guide rail is fixedly connected to the support frame 130, so that the slider can be driven by the driving motor to move in a straight line along the guide rail so as to realize pulling and pushing of the chip carrier 110. For example, the driving motor may be a stepping motor. Certainly, the embodiments of the present disclosure are not limited in this aspect, the reaction device 10 may not be provided with a driving motor, and the chip carrier 110 can be pulled out or pushed into the support frame 130 by manual operation, thereby reducing cost and weight of the device.

For example, the bottom plate 111 includes a hollow region 111a, and the support portion 112 is located in the hollow region 111a of the bottom plate 111 and is configured to support the detection chip. For example, the size of the support portion 112 is smaller than the size of the hollow region 111a, so that a part of the surface area of the detection chip is exposed to the air after the detection chip is placed on the support portion 112, so as to facilitate heat loss of the detection chip and temperature control. For example, the size of the support portion 112 may be determined according to actual requirements, for example, according to the stability of placement of the detection chip and the heat dissipation requirements, and the embodiments of the present disclosure are not limited in this aspect.

For example, the limiting groove 113 is located around the hollow region 111a of the bottom plate 111, and is configured to prevent shift of the detection chip. For example, the size of the limiting groove 113 is equal to or substantially the same as the size of the detection chip, so as to better provide a limiting function and prevent the detection chip from easily sliding out of the limiting groove 113. Certainly, the embodiments of the present disclosure are not limited in this aspect, and the size of the limiting groove 113 may also be slightly larger than the size of the detection chip, which may be determined according to actual requirements. For example, the shape of the limiting groove 113 is approximately rectangular, so that it is convenient to place a rectangular detection chip therein. For example, the limiting groove 113 can also provide a support function, and supports the detection chip together with the support portion 112. For example, in order to provide space for manual operation and facilitate the user to grasp the detection chip, a set of opposite edges of the limiting groove 113 can be set to have arc shapes, and the arc shapes protrude away from each other, so that operating space is reserved for the user's fingers and it is convenient for the user to grasp the detection chip, thereby facilitating the placement or removal of the detection chip.

For example, the limiting block 114 is located on at least one side of the limiting groove 113 and is configured to prevent warping of the detection chip. The amount of limiting blocks 114 is not limited. Although the case of two limiting blocks 114 is illustrated in FIG. 3, this case does not constitute a limitation to the embodiments of the present disclosure. For example, the amount of limiting blocks 114 may also be one, three, or any other values. The position of the limiting block 114 is not limited. Although the limiting blocks 114 illustrated in FIG. 3 are located on the same side of the limiting groove 113, this case does not constitute a limitation to the embodiments of the present disclosure. For example, a plurality of limiting blocks 114 may also be located on different sides of the limiting groove 113, as long as the limiting blocks 114 can prevent warping of the detection chip. For example, in the case where the detection chip is placed on the chip carrier 110, the detection chip needs to be fixed with a clamp, and the contact electrode of the clamp needs to be in contact with the control electrode of the detection chip, so that the detection chip is prone to warp under the pressure of the clamp. By providing the limiting block 114, the detection chip can be prevented from warping, so that the connection between the detection chip and the clamp is stronger. Detailed description of the clamp and the contact electrode may be referred to the following content, which may not be described in detail herein.

Figure 4:
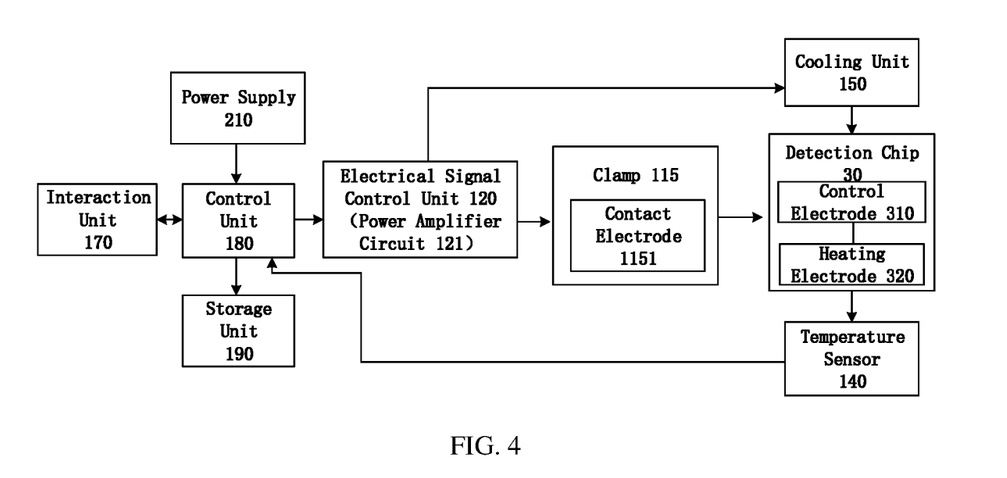
FIG. 4 is a schematic block diagram of components of a reaction device provided by some embodiments of the present disclosure.

FIG. 4 is a schematic block diagram of components of a reaction device provided by some embodiments of the present disclosure. As illustrated in FIG. 4, the chip carrier 110 further includes a clamp 115, and the clamp 115 is configured to be capable of moving close to or away from the support portion 112 so as to allow the detection chip to be at a fixed position or a variable position relative to the support portion 112. For example, the detection chip may be the detection chip 30 illustrated in FIG. 4, and the detection chip 30 includes a control electrode 310 and a heating electrode 320. After the detection chip 30 is placed on the chip carrier 110, the clamp 115 can be provided close to the support portion 112, so that the detection chip 30 is fixed on the chip carrier 110. When the detection chip 30 needs to be taken out, the clamp 115 is moved away from the support portion 112, so that the detection chip 30 can be taken out from the chip carrier 110. For example, the distance between the clamp 115 and the support portion 112 may be adjusted manually to allow the clamp 115 to move relative to the support portion 112, or the distance between the clamp 115 and the support portion 112 can be adjusted by a separate drive component (such as a motor). The embodiments of the present disclosure are not limited in this aspect. For example, in some examples, the clamp 115 may be disposed inside the support frame 130 and located above the chip carrier 110, and can move up and down relative to the chip carrier 110.

For example, the clamp 115 includes a contact electrode 1151, and the contact electrode 1151 is configured to be capable of being contact-connected with the control electrode 310 of the detection chip 30 so as to achieve electrical connection. After the detection chip 30 is placed on the chip carrier 110, the detection chip 30 is fixed by the clamp 115. For example, the clamp 115 and the detection chip 30 are in contact with each other, so that the contact electrode 1151 and the control electrode 310 are also connected in contact, so as to transmit the electrical signal. For example, the contact electrode 1151 can be made of a metal material, so that the resistance can be reduced and the requirements for the signal driving capability can be reduced. For example, the clamp 115 may also include a clamping structure, and the contact electrode 1151 may be provided on the clamping structure, for example, on the surface where the clamping structure contacts the detection chip 30, so as to realize contact connection of the contact electrode 1151 and the control electrode 310 in the detection chip 30. For example, the clamping structure may be a general clamp (for example, a vise, a chuck, a suction cup, etc.) or a special clamp (for example, a structure specially designed for the reaction device 10), and the embodiments of the present disclosure are not limited in this aspect.

For example, the electrical signal control unit 120 may be a power amplifier circuit 121 illustrated in FIG. 4, and the power amplifier circuit 121 can output a voltage signal with a higher power, which can directly drive the load, and has strong loading capacity. Certainly, the embodiments of the present disclosure are not limited in this aspect, and the electrical signal control unit 120 may also adopt other suitable circuits or modules. The electrical signal control unit 120 is electrically connected to the contact electrode 1151 and is configured to apply an electrical signal to the control electrode 310 of the detection chip 30 through the contact electrode 1151 so as to drive the heating electrode 320 of the detection chip 30. For example, the electrical signal output by the electrical signal control unit 120 is transmitted to the contact electrode 1151 through the electrical wire. Because the contact electrode 1151 is in contact with the control electrode 310, the electrical signal is transmitted to the control electrode 310 and then is transmitted to the heating electrode 320. The heating electrode 320 generates and releases heat under the action of the electrical signal, so that the temperature of the detection chip 30 rises, thereby realizing the heating function.

For example, as illustrated in FIG. 4, the reaction device 10 further includes a temperature sensor 140, and the temperature sensor 140 is configured to be capable of being in contact with the detection chip 30 so as to sense the temperature of the detection chip 30. For example, as illustrated in FIG. 3, the support portion 112 includes a groove 1121, and the temperature sensor 140 is located in the groove 1121 (the temperature sensor 140 is not illustrated in FIG. 3). In the case where the detection chip 30 is placed on the chip carrier 110, the temperature sensor 140 is in direct contact with the detection chip 30, and therefore, the temperature of the detection chip 30 can be sensed by the temperature sensor 140. It should be noted that, in the embodiments of the present disclosure, the temperature sensor 140 may not directly contact the detection chip 30, but may have a certain gap from the detection chip 30. The specific setting method of the temperature sensor 140 may be determined according to actual requirements, for example, according to the type of the temperature sensor 140, and the embodiments of the present disclosure are not limited in this aspect.

For example, the temperature sensor 140 may be various types of temperature sensors, for example, a contact-type temperature sensor or a non-contact-type temperature sensor, etc., such as a thermocouple temperature sensor or an infrared temperature sensor. For example, in some examples, the temperature sensor 140 is a digital temperature sensor, the model is DS18B20, which has advantages of small size, low hardware overhead, strong anti-interference ability, high accuracy, etc. It should be noted that, in some embodiments of the present disclosure, in the case where the detection chip 30 includes a temperature sensor, there is no need to provide a temperature sensor 140 in the reaction device 10.

For example, as illustrated in FIG. 4, the reaction device 10 further includes a cooling unit 150, and the cooling unit 150 is configured to cool down the detection chip 30. For example, the cooling unit 150 may be a fan or an air blower, such as a program-controllable fan or a program-controllable air blower, so as to reduce the cost while realizing the cooling function. For example, the cooling unit 150 is provided above or below the chip carrier 110, so that the heat dissipation can be accelerated. In the case where the detection chip 30 needs to be cooled down, the cooling unit 150 is used to achieve air cooling, so that the temperature of the detection chip 30 is reduced. For example, through the cooperation of the electrical signal control unit 120 and the cooling unit 150, the temperature of the detection chip 30 can be risen or reduced as required, thereby achieving temperature control and allowing the reaction system solution in the detection chip 30 to perform temperature cycle of refolding-annealing-extending, so as to implement amplification reaction.

Figure 5:
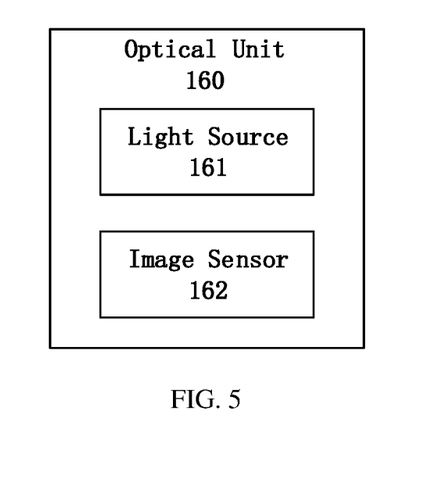
FIG. 5 is a schematic block diagram of an optical unit of a reaction device provided by some embodiments of the present disclosure.

For example, the reaction device 10 further includes an optical unit 160, and the optical unit 160 is configured to perform an optical detection on the detection chip 30. As illustrated in FIG. 5, the optical unit 160 includes a light source 161 and an image sensor 162. For example, the light source 161 is configured to emit light to illuminate the detection chip 30, and the image sensor 162 is configured to receive light emitted by the light source 161 and reflected by the detection chip 30. For example, the light source 161 may be a laser (for example, the wavelength of the laser is 450 nm to 480 nm) or a fluorescent lamp, and the image sensor 162 may be a charge coupled device (CCD) image sensor, which is not limited in the embodiments of the present disclosure. After the reaction system solution in the detection chip 30 completes the amplification reaction, the optical unit 160 is used to perform the optical detection, so that a fluorescent image can be obtained and the PCR detection result can be obtained.

For example, as illustrated in FIG. 2 and FIG. 4, the reaction device 10 further includes an interaction unit 170, and the interaction unit 170 is configured to interact with the user. For example, the interaction unit 170 may be a touch screen, and the touch screen is configured to display and perform a touch detection to obtain an input instruction of the user. For example, the touch screen may be a liquid crystal display (LCD) touch screen, an organic light-emitting diode (OLED) touch screen, a quantum dot light-emitting diode (QLED) touch screen, an electronic paper touch screen, etc., and the embodiments of the present disclosure are not limited in this aspect. The interaction unit 170 may also be other forms of components, such as a button, a display screen, a voice input device, etc., as long as the interaction unit 170 can interact with the user.

For example, as illustrated in FIG. 4, the reaction device 10 further includes a control unit 180, and the control unit 180 is configured to control the working state of the reaction device 10. For example, the control unit 180 may run a control program to allow the electrical signal control unit 120 to output the electrical signal, control the cooling unit 150 to work, receive the detection signal transmitted by the temperature sensor 140, control the interaction unit 170 to display, and receive the instruction input by the user through the interaction unit 170, and the control unit 180 may also have other functions, which are not limited in the embodiments of the present disclosure. For example, the control unit 180 may be a central processing unit (CPU), a single-chip microcontroller unit (MCU), a digital signal processor (DSP), a field programmable gate array (FPGA), or the like, which is not limited in the embodiments of the present disclosure. For example, in some examples, the control unit 180 is an STM32 microcontroller unit.

For example, as illustrated in FIG. 2 and FIG. 4, the reaction device 10 further includes a storage unit 190, and the storage unit 190 is configured to store detected data and/or the work log of the reaction device 10, etc. For example, the storage unit 190 may be disposed in a movable installation groove 131 on the side of the support frame 130, so that the movable installation groove 131 can be easily pulled out or pushed into the support frame 130, so as to realize the installation or removal of the storage unit 190. For example, the storage unit 190 may be various forms of computer-readable storage media, such as volatile memory and/or non-volatile memory. For example, the volatile memory may include random access memory (RAM) and/or cache memory. For example, the non-volatile memory may include read only memory (ROM), hard disk, erasable programmable read only memory (EPROM), portable compact disk read only memory (CD-ROM), USB memory, SD card, flash memory, etc. For example, the storage unit 190 can store the detected data, such as the fluorescent image and the analysis result, so that the detection result can be copied and transmitted conveniently. The storage unit 190 may also be used to store the data generated by the reaction device 10, such as the work log of the reaction device 10, the instruction input by the user, or the like, which is not limited in the embodiments of the present disclosure.

For example, as illustrated in FIG. 4, the reaction device 10 further includes a power supply 210, and the power supply 210 is configured to supply power to the reaction device 10. For example, the power supply 210 may be an interface of an external power source, which is electrically connected to the power supply network through a wire, a transformer, etc., or may be a built-in power source, such as a secondary battery (such as a lithium battery), a primary battery (such as an alkaline battery), a solar battery, or any other applicable power supply components, which is not limited in the embodiments of the present disclosure.

Figure 6A:
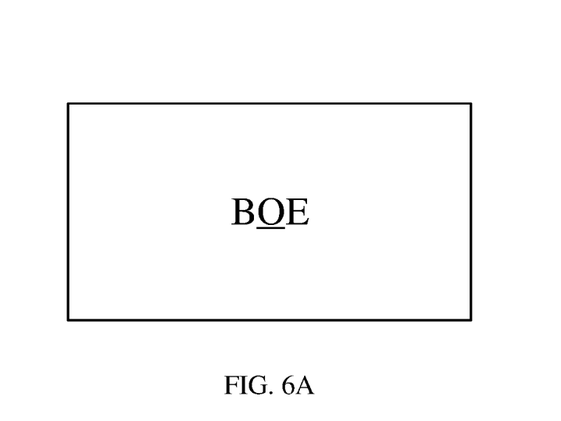
FIGS. 6A-6D are schematic diagrams of operation interfaces of a reaction device provided by some embodiments of the present disclosure.
Figure 6B:
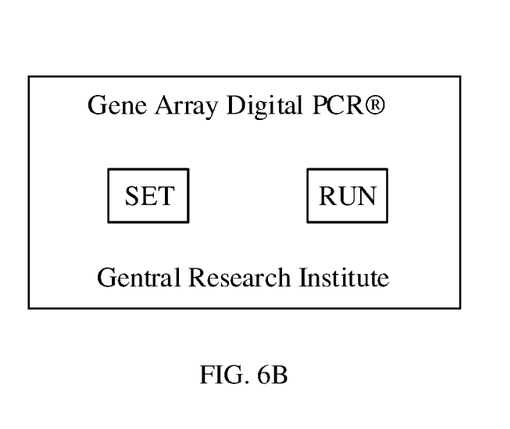
Figure 6C:
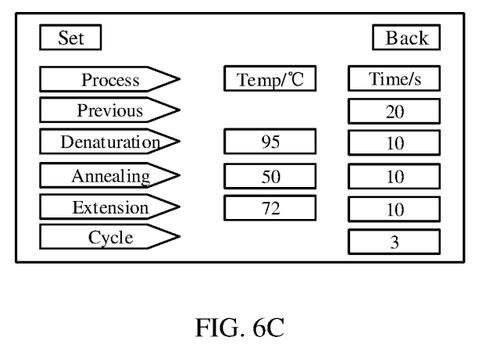
Figure 6D:
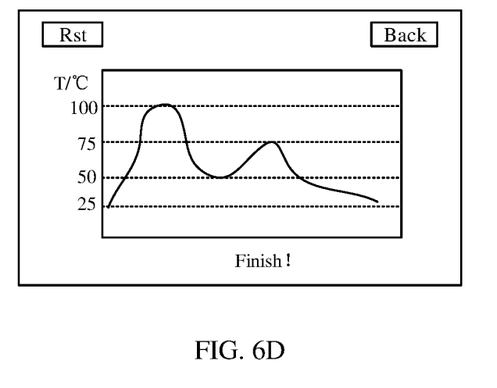

FIGS. 6A-6D are schematic diagrams of operation interfaces of a reaction device provided by some embodiments of the present disclosure. FIG. 6A is a welcome interface, FIG. 6B is a function selecting interface, FIG. 6C is a parameter setting interface, and FIG. 6D is a temperature curve monitoring interface. For example, in the function selecting interface, the user may select "SET" to enter the parameter setting interface, or select "RUN" to execute the temperature cycling process and enter the temperature curve monitoring interface. For example, in the parameter setting interface, the user can set the temperature of each phase of the temperature cycling process, such as the temperature of the refolding phase, the temperature of the annealing phase, and the temperature of the extending phase, and the user can set the duration of each phase and the number of temperature cycles as well.

It should be noted that the operation interfaces illustrated in FIGS. 6A-6D are only illustrative and not limitative, the reaction device 10 can run the corresponding control program according to actual needs and has multiple operation interfaces, and the information presented by each operation interface can be determined according to actual needs. For example, in some examples, the control program may include three subroutines, which include an operating system, an optical detection software, an image merging and data reading software, so as to realize functions such as temperature cycling and optical detection. For example, the control program may be stored in the storage unit 190 illustrated in FIG. 4 and executed by the control unit 180, and the control unit 180 displays the operation interface of the control program in the interaction unit 170.

Figure 7:
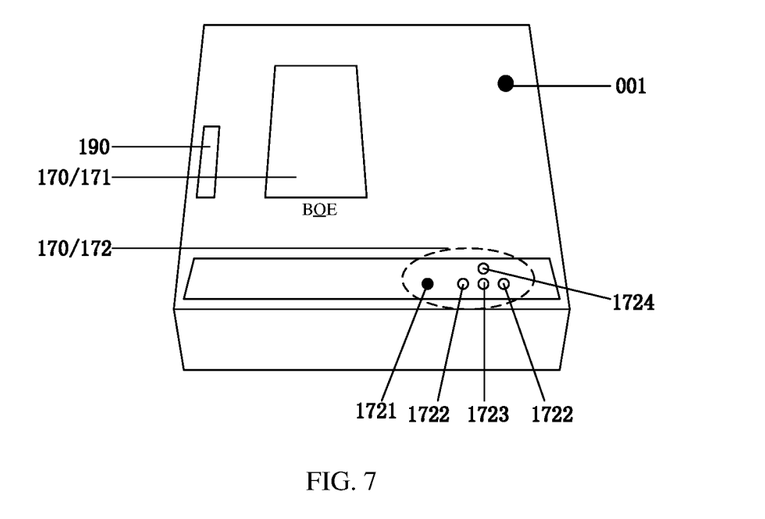
FIG. 7 is a first schematic diagram of appearance of another reaction device provided by some embodiments of the present disclosure.
Figure 8:
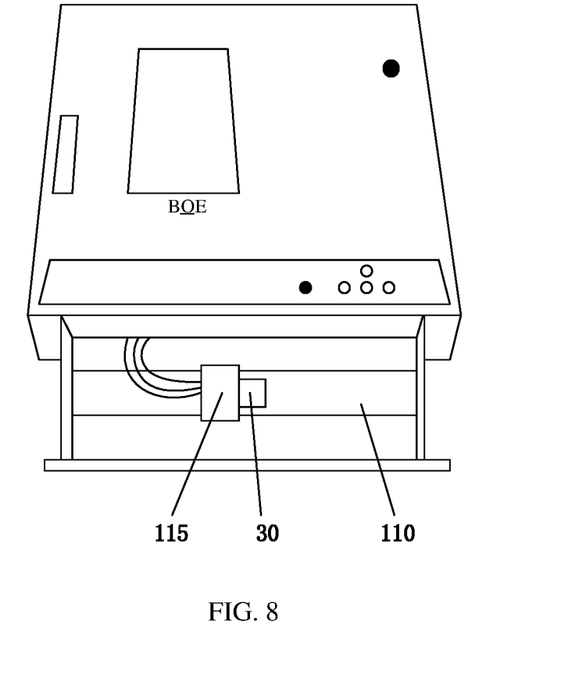
FIG. 8 is a second schematic diagram of appearance of another reaction device provided by some embodiments of the present disclosure.

FIG. 7 is a first schematic diagram of appearance of another reaction device provided by some embodiments of the present disclosure, and FIG. 8 is a second schematic diagram of appearance of another reaction device provided by some embodiments of the present disclosure. As illustrated in FIG. 7 and FIG. 8, the reaction device 10 of this embodiment is basically the same as the reaction device 10 illustrated in FIG. 2 to FIG. 4 except that the implementation of the interaction unit 170 and the appearance of the reaction device 10 are different.

In this embodiment, the interaction unit 170 includes a display screen 171 and buttons 172. The display screen 171 is configured to display, and may be, for example, an LCD display screen, an OLED display screen, a QLED display screen, an electronic paper display screen, etc., which is not limited in the embodiments of the present disclosure. The button 172 is configured to obtain the user's input instruction, and may be a mechanical button, an optical button, a touch button, etc., which is not limited in the embodiments of the present disclosure. For example, the buttons 172 may include a program control switch 1721, a parameter setting button 1722, a confirmation button 1723, and a reset and step selection button 1724. For example, various parameters in the detection process can be set through the parameter setting button 1722, such as temperature, time, etc.; and the detection step in the detection process can be selected through the reset and step selection button 1724. For example, the reaction device 10 further includes a power switch 001, and the power switch 001 is used to control the reaction device 10 to turn on or turn off. It should be noted that in the embodiments of the present disclosure, the number, setting positions, and functions of the buttons 172 are not limited, which can be determined according to actual needs. The actual setting of the buttons 172 can be, for example, based on the program running in the reaction device 10, and therefore, the buttons 172 cooperate with the program to realize the interaction between the user and the reaction device 10.

For example, the storage unit 190 is disposed in an openable and closeable installation groove on the upper surface of the reaction device 10, and the openable and closeable installation groove can be opened to allow the storage unit 190 to be easily inserted or taken out. For example, the chip carrier 110 may be pulled out or pushed in, and the detection chip 30 may be placed on the chip carrier 110 and fixed by the clamp 115.

It should be noted that, in the embodiments of the present disclosure, the reaction device 10 may include more or fewer components, which may be determined according to the actual function and performance required to be realized, and the embodiments of the present disclosure do not limit this. The various components described above, such as the chip carrier 110, the electrical signal control unit 120, the support frame 130, the temperature sensor 140, the cooling unit 150, the optical unit 160, the interaction unit 170, the control unit 180, the storage unit 190, and the power supply 210, can be implemented in any suitable manner, as long as the corresponding function can be implemented, which is not limited to the implementation manner described above.

At least one embodiment of the present disclosure further provides a reaction system, and the reaction system includes at least one detection chip and the reaction device described in any one of the embodiments of the present disclosure that can be used in combination with the at least one detection chip. The reaction system can realize high-efficiency and accurate temperature control, simple temperature control mode, direct insertion and direct reading, simple operation, high intelligent degree, high portable degree, high integration degree, and high detection efficiency, and can realize efficient and fast digital PCR detection.

Figure 9:
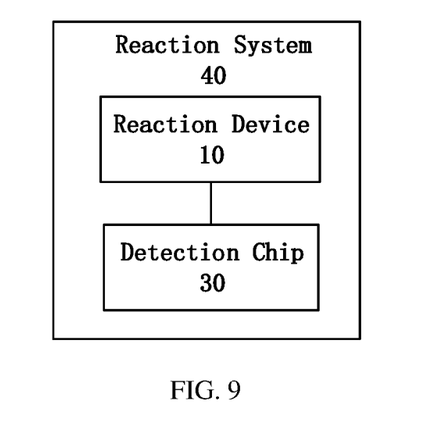
FIG. 9 is a schematic block diagram of a reaction system provided by some embodiments of the present disclosure.
Figure 10:
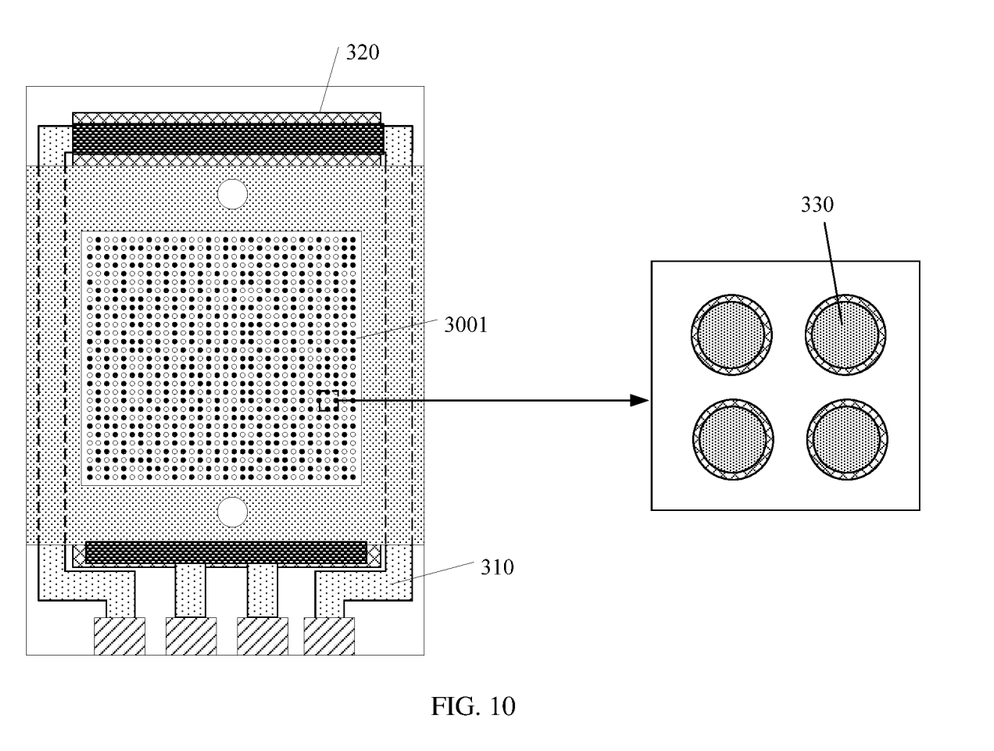
FIG. 10 is a schematic planar view of a detection chip of a reaction system provided by some embodiments of the present disclosure.

FIG. 9 is a schematic block diagram of a reaction system provided by some embodiments of the present disclosure. As illustrated in FIG. 9, a reaction system 40 includes a reaction device 10 and at least one detection chip 30. For example, the reaction device 10 is the reaction device described in any one of the embodiments of the present disclosure. The reaction system 40 may include one or more detection chips 30. For example, the detection chips 30 may be any one of the aforementioned detection chips, and the specifications of the detection chips may be the same or different from each other. For example, as illustrated in FIG. 10, the detection chip 30 includes a plurality of micro-reaction chambers 330, and the micro-reaction chambers 330 can contain the reaction system solution. For example, in some examples, the detection chip 30 has reaction units of 400,000 level, that is, micro-reaction chambers 330 of 400,000 level. The control electrode 310 of the detection chip 30 can receive the electrical signal and transmit the electrical signal to the heating electrode 320. The heating electrode 320 generates and releases heat under the action of the electrical signal, so that the functional region 3001 of the detection chip 30 is heated. The electrical signal control unit 120 of the reaction device 10 applies the electrical signal to the detection chip 30 to drive the heating electrode 320 of the detection chip 30, so as to heat up the detection chip 30, and the cooling unit 150 of the reaction device 10 cools down the detection chip 30, so as to allow the reaction system solution to realize a temperature cycle including a refolding phase, an annealing phase, and an extending phase. For example, the optical unit 160 of the reaction device 10 may perform the optical detection on the detection chip 30 to obtain the fluorescent image.

For example, the process of the PCR thermal cycle amplification performed by the reaction system 40 is described below.

Figure 11A:
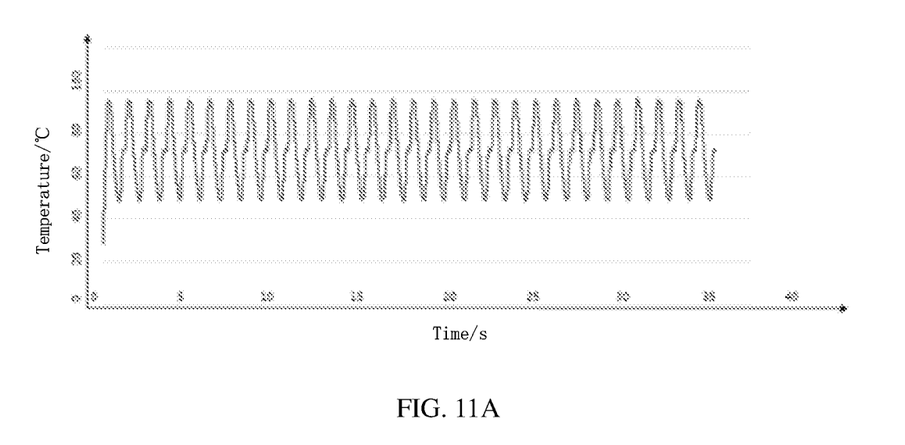
FIG. 11A is a temperature-to-time relationship curve of a reaction system during thermal cycle provided by some embodiments of the present disclosure.
Figure 11B:
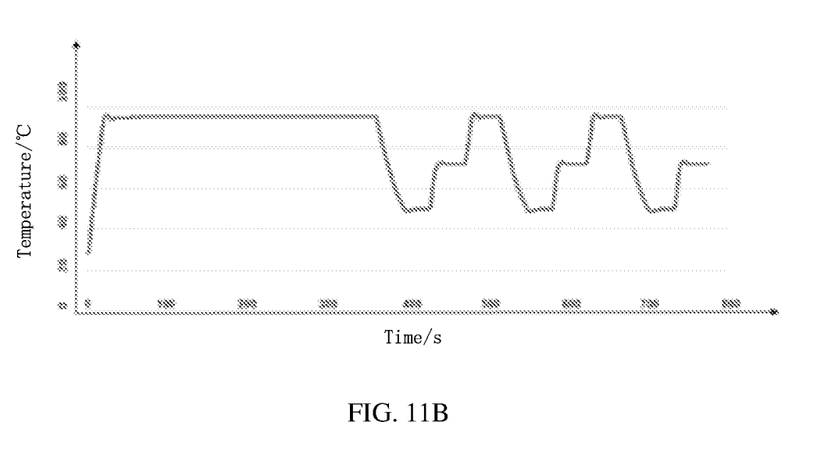
FIG. 11B is a temperature-to-time relationship curve of a reaction system during thermal cycle including a pre-refolding process provided by some embodiments of the present disclosure.

The detection chip 30 injected with the reaction system solution is placed on the chip carrier 110 of the reaction device 10 and is fixed by the clamp 115 to allow the contact electrode 1151 to be electrically connected to the control electrode 310 of the detection chip 30. The reaction device 10 is parameterized. For example, the cycle parameters include refolding at 95° C. for 15 seconds, annealing at 55° C. for 45 seconds, and extending at 72° C. for 45 seconds, and a total of 30 thermal cycles are set. For example, pre-refolding may be set at 95° C. for 5 minutes. The droplets containing template DNA in the micro-reaction chamber 330 in the detection chip 30 may perform PCR amplification reactions, while the droplets without template DNA in the micro-reaction chamber 330 serve as a control group. For example, the temperature-to-time relationship curve of thermal cycle is illustrated in FIG. 11A and FIG. 11B. It can be seen that the temperature control effect of thermal cycle is good, which can achieve precise temperature control, the temperature control accuracy reaches 0.5° C., the detection time is short (time for 30 cycles is 35 minutes), and the detection efficiency is high.

After the thermal cycle amplification is completed, the optical unit 160 of the reaction device 10 is used to perform optical detection on the detection chip 30 so as to obtain the fluorescent image. The reaction system 40 can allow the reaction system solution in the detection chip 30 to perform effective thermal cycle amplification, and can obtain clear fluorescent images, and the detection throughput is high.

It should be noted that in some embodiments of the present disclosure, the reaction system 40 may further include more components or parts, which are not limited in the embodiments of the present disclosure. Detailed description and technical effects of the reaction system 40 may be referred to the above description of the reaction device 10, and details are not described herein again.

The following statements need to be noted.

(1) The drawings of the embodiments of the present disclosure involve only the structures related to the embodiments of the present disclosure, and other structures may be referred to general design.

(2) In case of no conflict, the embodiments of the present disclosure and the features in the embodiments can be combined with each other to obtain new embodiments.

What have been described above merely are specific implementations of the present disclosure, but the protection scope of the present disclosure is not limited to this. The protection scope of the present disclosure is determined by the appended claims.

What is claimed is:

1. A reaction device for a detection chip, comprising:
   a chip carrier, configured to place and fix the detection chip;
   an electrical signal control unit, configured to apply an electrical signal to the detection chip so as to drive a heating electrode of the detection chip; and
   a support frame,
   wherein the chip carrier comprises a bottom plate, a support portion, a limiting groove, and at least one limiting block;
   the bottom plate comprises a hollow region, and is configured to be in sliding connection with the support frame;
   the support portion is in the hollow region of the bottom plate, and is configured to support the detection chip;
   the limiting groove is around the hollow region of the bottom plate, and is configured to prevent shift of the detection chip;
   the limiting block is on at least one side of the limiting groove, and is configured to prevent warping of the detection chip,
   wherein the chip carrier further comprises a clamp, and
   the clamp is configured to be capable of moving close to or away from the support portion, so as to allow the detection chip to be at a fixed position or a variable position relative to the support portion.

2. The reaction device according to claim 1, wherein the clamp comprises a contact electrode,
   the contact electrode is configured to be capable of being in contact with a control electrode of the detection chip to realize electrical connection, and
   the electrical signal control unit is electrically connected to the contact electrode, and is configured to apply the electrical signal to the control electrode of the detection chip through the contact electrode so as to drive the heating electrode of the detection chip.

3. The reaction device according to claim 1, wherein the bottom plate is further connected to the support frame through a linear guide rail.

4. The reaction device according to claim 1, further comprising a driving motor,
   wherein the driving motor is configured to drive the bottom plate to move relative to the support frame.

5. The reaction device according to claim 1, further comprising a temperature sensor,
   wherein the support portion comprises a groove, and the temperature sensor is in the groove, and is configured to be capable of being in contact with the detection chip so as to sense a temperature of the detection chip.

6. The reaction device according to claim 1, further comprising a cooling unit,
   wherein the cooling unit is configured to cool down the detection chip.

7. The reaction device according to claim 6, wherein the cooling unit comprises a fan or an air blower.

8. The reaction device according to claim 1, further comprising an optical unit,
   wherein the optical unit is configured to perform an optical detection on the detection chip.

9. The reaction device according to claim 8, wherein the optical unit comprises:
   a light source, configured to emit light to illuminate the detection chip; and
   an image sensor, configured to receive light emitted by the light source and reflected by the detection chip.

10. The reaction device according to claim 9, wherein the light source comprises a laser or a fluorescent lamp.

11. The reaction device according to claim 9, wherein the image sensor comprises a charge coupled device image sensor.

12. The reaction device according to claim 1, further comprising an interaction unit,
    wherein the interaction unit is configured to interact with a user.

13. The reaction device according to claim 12, wherein the interaction unit comprises a touch screen, and the touch screen is configured to display and perform a touch detection to obtain an input instruction of the user; or
    the interaction unit comprises a display screen and a button, the display screen is configured to display, and the button is configured to obtain an input instruction of the user.

14. The reaction device according to claim 1, further comprising a control unit,
    wherein the control unit is configured to control a working state of the reaction device.

15. The reaction device according to claim 1, further comprising a storage unit,
    wherein the storage unit is configured to store detected data and/or a work log of the reaction device.

16. The reaction device according to claim 1, further comprising a power supply,
    wherein the power supply is configured to supply power to the reaction device.

17. A reaction system, comprising the reaction device for the detection chip according to claim 1 and at least one detection chip,
    wherein the detection chip comprises a plurality of micro-reaction chambers, and the micro-reaction chambers are capable of containing reaction system solution; and
    the electrical signal control unit of the reaction device is configured to apply the electrical signal to the detection chip to heat up the detection chip, and a cooling unit of the reaction device is configured to cool down the detection chip, so as to allow the reaction system solution to perform temperature cycle comprising a refolding phase, an annealing phase, and an extending phase.

18. The reaction system according to claim 17, wherein an optical unit of the reaction device is configured to perform an optical detection on the detection chip so as to obtain a fluorescent image.

\* \* \* \* \*